US012562255B2

(12) United States Patent
Venkataraman et al.

(10) Patent No.: US 12,562,255 B2
(45) Date of Patent: Feb. 24, 2026

(54) USING MULTIPLE MODALITIES OF SURGICAL DATA FOR COMPREHENSIVE DATA ANALYTICS OF A SURGICAL PROCEDURE

(71) Applicant: Verb Surgical Inc., Santa Clara, CA (US)

(72) Inventors: Jagadish Venkataraman, Menlo Park, CA (US); Pablo Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/596,298

(22) Filed: Mar. 5, 2024

(65) Prior Publication Data

US 2024/0290459 A1 Aug. 29, 2024

Related U.S. Application Data

(63) Continuation of application No. 17/493,589, filed on Oct. 4, 2021, now Pat. No. 11,935,641, which is a
(Continued)

(51) Int. Cl.
 *G16H 20/40* (2018.01)
 *G06F 16/45* (2019.01)
 (Continued)

(52) U.S. Cl.
 CPC ............. *G16H 20/40* (2018.01); *G06F 16/45* (2019.01); *G16H 30/40* (2018.01); *G16H 40/40* (2018.01)

(58) Field of Classification Search
 CPC ........ G16H 40/63; G16H 40/20; G16H 30/40; G16H 80/00; G16H 15/00; G16H 40/60; G16H 40/40; G16H 40/00
 See application file for complete search history.

(56) References Cited

U.S. PATENT DOCUMENTS 9,836,654 B1    12/2017  Alvi et al.
2008/0062280 A1  3/2008  Wang et al.
(Continued)

FOREIGN PATENT DOCUMENTS

CN      105992996 A    10/2016
JP      2011-167301 A   9/2011
(Continued)

OTHER PUBLICATIONS

Volkov, Mikhail, et al. "Machine learning and coresets for automated real-time video segmentation of laparoscopic and robot-assisted surgery." 2017 IEEE international conference on robotics and automation (ICRA). IEEE, 2017 (Year: 2017).*
(Continued)

*Primary Examiner* — Jason B Dunham
*Assistant Examiner* — Constantine Siozopoulos
(74) *Attorney, Agent, or Firm* — Aikin & Gallant, LLP

(57) ABSTRACT

This patent disclosure provides various embodiments of combining multiple modalities of non-text surgical data in forms of videos, images, and audios in a meaningful manner so that the combined data can be used to perform comprehensive data analytics for a surgical procedure. In some embodiments, the disclosed system can begin by receiving two or more modalities of surgical data during the surgical procedure. The system then time-synchronizes the two or more modalities of surgical data to generate two or more modalities of time-synchronized surgical data. Next, the system converts each modality of the time-synchronized surgical data into a corresponding array of values of a common format. The system then combines the two or more arrays of values to generate a combined set of values. The system subsequently performs comprehensive data analytics on the combined set of values to generate a surgical decision for the surgical procedure.

20 Claims, 4 Drawing Sheets

Related U.S. Application Data continuation of application No. 16/418,790, filed on May 21, 2019, now Pat. No. 11,139,062.

(51) Int. Cl.
  *G16H 30/40*          (2018.01)
  *G16H 40/40*          (2018.01)

(56)                    References Cited

U.S. PATENT DOCUMENTS

| | | | |
|---|---|---|---|
| 2011/0273309 | A1 | 11/2011 | Zhang et al. |
| 2013/0041685 | A1 | 2/2013 | Yegnanarayanan |
| 2015/0164436 | A1 | 6/2015 | Maron et al. |
| 2016/0342744 | A1 | 11/2016 | Joao |
| 2017/0019529 | A1 | 1/2017 | Bostick et al. |
| 2018/0122506 | A1 * | 5/2018 | Grantcharov ........... G06F 17/40 |
| 2019/0206562 | A1 | 7/2019 | Shelton, IV et al. |
| 2020/0273581 | A1 * | 8/2020 | Wolf ...................... G16H 40/63 |

FOREIGN PATENT DOCUMENTS

| | | | |
|---|---|---|---|
| KR | 10-2011-0092350 | A | 8/2011 |
| KR | 10-1881862 | B1 | 7/2018 |
| WO | WO-2017075541 | A1 * 5/2017 | ............ A61B 17/00 |
| WO | 2017220788 | A1 | 12/2017 |

OTHER PUBLICATIONS

Office Action received for Korean Patent Application No. 10-2021-7040698, mailed on Mar. 20, 2024, 18 pages (6 pages of English Translation and 12 pages of Original Document).

Office Action received for Chinese Patent Application No. 201980096658.8, mailed on Mar. 12, 2025, 20 pages (11 Pages of Original Document and 9 Pages of English Translation).

Second Office Action received for Chinese Patent Application No. 201980096658.8, mailed on Jun. 19, 2025, 19 pages (11 Pages of Original Document and 8 Pages of English Translation).

Song et al., "Principles and Application Technology of Sensors," Southwest Jiaotong University Press, pp. 277-278 (2 Pages of Original Document and 3 Pages of English Translation) pp. 277-278.

First Office Action received for Chinese Patent Application No. 201980096658.8, mailed Mar. 12, 2025, 22 pages (11 Pages of Original Document and 11 Pages of English Translation).

Non-Final Office Action received for U.S. Appl. No. 16/418,790, mailed on Dec. 30, 2020, 24 pages.

International Search Report and Written Opinion for International Application No. PCT/US2019/034063 mailed Feb. 21, 2020, 10 pages.

International Preliminary Report on Patentability for International Application No. PCT/US2019/034063 mailed Dec. 2, 2021, 6 pages.

Extended European Search Report for European Application No. 19929554.4 mailed Dec. 21, 2022, 7 pages.

Merloz, Phillippe, et al; "Basic Concept in Computer Assisted Surgery"; Chinese Journal of Reparative and Reconstructive Surgery, vol. 20 (3), 2006, 99-276-278.

Notice of Allowance received for Korean Application No. 10-2021-7040698, mailed on Jun. 17, 2024, 3 pages (2 pages of original office action and 1 page of English Translation).

\* cited by examiner

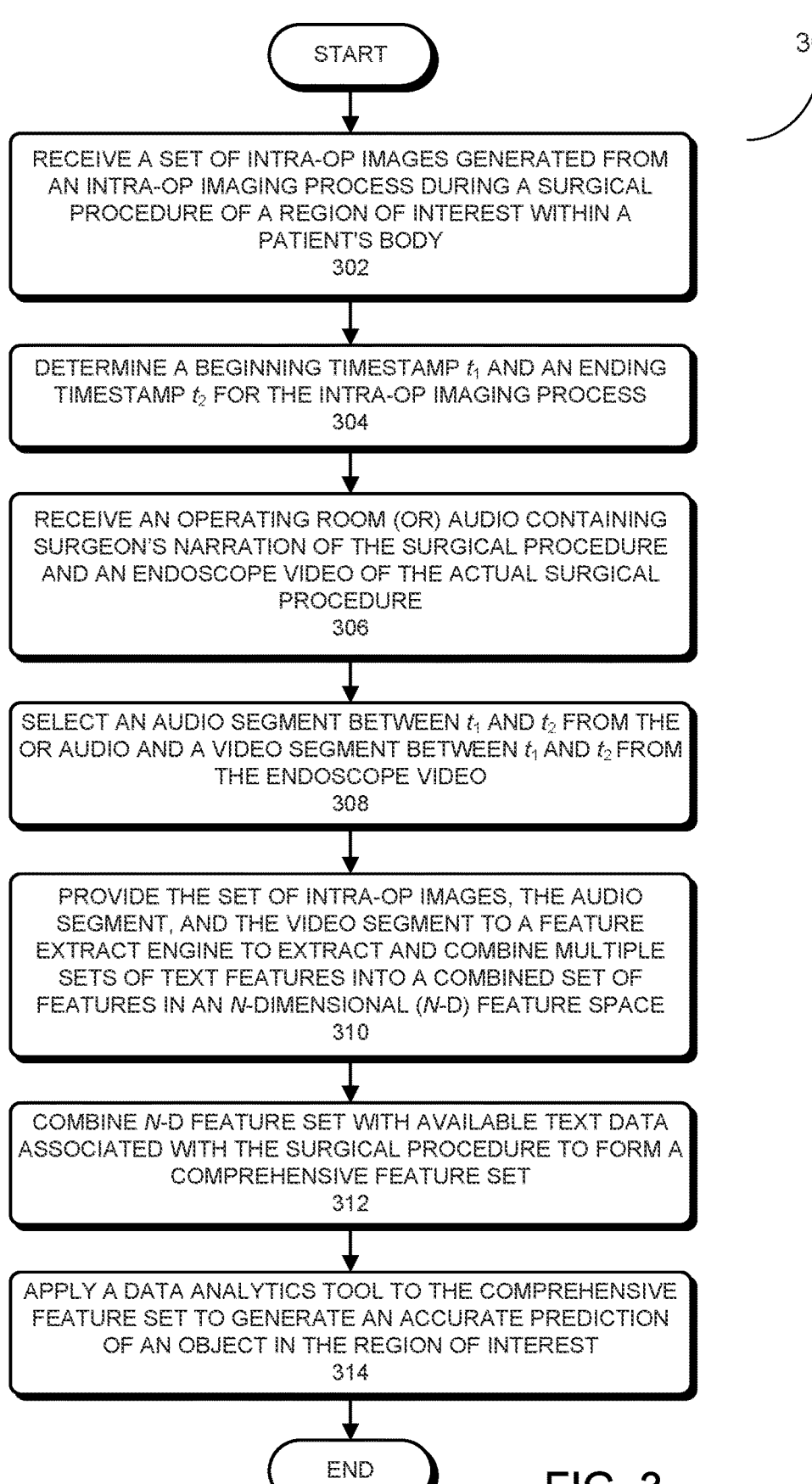

300

START

RECEIVE A SET OF INTRA-OP IMAGES GENERATED FROM AN INTRA-OP IMAGING PROCESS DURING A SURGICAL PROCEDURE OF A REGION OF INTEREST WITHIN A PATIENT'S BODY
302

DETERMINE A BEGINNING TIMESTAMP $t_1$ AND AN ENDING TIMESTAMP $t_2$ FOR THE INTRA-OP IMAGING PROCESS
304

RECEIVE AN OPERATING ROOM (OR) AUDIO CONTAINING SURGEON'S NARRATION OF THE SURGICAL PROCEDURE AND AN ENDOSCOPE VIDEO OF THE ACTUAL SURGICAL PROCEDURE
306

SELECT AN AUDIO SEGMENT BETWEEN $t_1$ AND $t_2$ FROM THE OR AUDIO AND A VIDEO SEGMENT BETWEEN $t_1$ AND $t_2$ FROM THE ENDOSCOPE VIDEO
308

PROVIDE THE SET OF INTRA-OP IMAGES, THE AUDIO SEGMENT, AND THE VIDEO SEGMENT TO A FEATURE EXTRACT ENGINE TO EXTRACT AND COMBINE MULTIPLE SETS OF TEXT FEATURES INTO A COMBINED SET OF FEATURES IN AN $N$-DIMENSIONAL ($N$-D) FEATURE SPACE
310

COMBINE $N$-D FEATURE SET WITH AVAILABLE TEXT DATA ASSOCIATED WITH THE SURGICAL PROCEDURE TO FORM A COMPREHENSIVE FEATURE SET
312

APPLY A DATA ANALYTICS TOOL TO THE COMPREHENSIVE FEATURE SET TO GENERATE AN ACCURATE PREDICTION OF AN OBJECT IN THE REGION OF INTEREST
314

END

FIG. 3

USING MULTIPLE MODALITIES OF SURGICAL DATA FOR COMPREHENSIVE DATA ANALYTICS OF A SURGICAL PROCEDURE

PRIORITY CLAIM AND RELATED PATENT APPLICATIONS

This patent application is continuation of, and hereby claims the benefit of priority under 35 U.S.C. § 120 to co-pending U.S. patent application Ser. No. 17/493,589, filed 4 Oct. 2021, entitled "USING MULTIPLE MODALITIES OF SURGICAL DATA FOR COMPREHENSIVE DATA ANALYTICS OF A SURGICAL PROCEDURE," expected to issue as U.S. Pat. No. 11,935,641, on 19 Mar. 2024, which is a continuation of, and hereby claims the benefit of priority under 35 U.S.C. § 120 to U.S. patent application Ser. No. 16/418,790, filed on 21 May 2019, now U.S. Pat. No. 11,139,062, issued 5 Oct. 2021, entitled "METHOD AND SYSTEM FOR COMBINING VIDEO, IMAGE, AND AUDIO DATA WITH TEXT DATA FOR COMPREHENSIVE DATA ANALYTICS," by inventors Jagadish Venkataraman and Pablo G. Kilroy. The above-listed applications are hereby incorporated by reference as a part of this patent document.

TECHNICAL FIELD

The present disclosure generally relates to building surgical data analytics tools and, more specifically, to systems, devices and techniques for combining video, image, and audio data collected during a surgical procedure with text data for comprehensive surgical data analytics.

BACKGROUND

Data analytics tools are designed to combine data from numerous data sources and to present and visualize the combined data in a specific manner to meet a user's demand. Most of the existing data analytics tools are optimized for row-based data entry and column-based dimensionality filtering. Based on such designs, the existing data analytics tools are able to generate measures, metrics, patterns, comparisons from the combined data. Nowadays, the functionalities of the existing data analytics tools are becoming increasingly scalable to the size of the data, which allow for seamless visualization and decision making regardless of the size of the data.

However, the existing data analytics tools have such a limitation that they can only perform analyses on alphanumeric or text data. Meanwhile, there are plenty of applications that generate information which is not just in text format, but can be in the forms of images, videos and audios. One example of such applications is surgery. During both the preoperative (or "pre-op" hereinafter) phase and the intraoperative (or "intra-op" hereinafter) phase of a surgery procedure, plenty of text data can be generated, such as patient vitals, patient information, surgeon information, and hospital statistics, among others. However, information generated during a pre-op physical of the surgery can be in the form of images; and information generated during the intra-op phase, i.e., during the actual surgery procedure can include clinical photos and snapshots of radiographs in the form of images, procedure data in the form of videos, and surgeon narrations/conversations in the form of audios. All these forms of non-text data are valuable information that can play a significant role in determining surgery performances such as patient outcomes, procedure durations, and hospital costs, among others. Unfortunately, the existing data analytics tools are not capable of performing comprehensive data analyses by combining text data and non-text data generated from a surgery procedure.

SUMMARY

This patent disclosure provides various embodiments of combining multiple modalities of non-text data of different formats, in particular in forms of videos, images, and audios in a meaningful manner so that the combined data from the multiple modalities are compatible with text data. In some embodiments, the combined data includes a set of N text features in an N-dimensional feature space. For example, for surgical applications, the set of N text features can include a set of surgical metrics/measurements in text format. Next, the combined data can be further combined with available text data from various sources to generate a comprehensive data set which can be understood and processed by text-based data analytics tools.

In some embodiments, before combining the multiple modalities of non-text data with text data, each modality of data in the multiple modalities is first segmented and converted to a set of text features. In one or more embodiments, a different machine-learning-based segmentation engine can be constructed to perform the corresponding data segmentation and conversion for a different modality of data. For a particular application, such as a surgical application, there can be at least three segmentation engines designed for three commonly known modalities, i.e., video data, image data, and audio data, respectively.

In some embodiments, once a given modality of data has been converted to a set of corresponding text features, the set of text features can be combined with other sources of text data, including text features converted from other modalities of non-text data and original text data. Once all of the available modalities of data have been converted to the text features and combined with other sources of text data, the combined feature set can then be used to perform a comprehensive data analytics using existing text-based data analytics tools. By supplementing the original text data with the multiple modalities of non-text data, the outputs from data-analytics tools, such as predictions or decisions generated based on the proposed comprehensive data analytics techniques can be significantly more accurate than the predictions or decisions generated based on analyzing just one modality of data or just the text data alone.

In one aspect, a process for performing comprehensive data analytics for a surgical procedure is disclosed. This process can begin by receiving two or more modalities of surgical data acquired from multiple data sources during a surgical procedure. The process then time-synchronizes the two or more modalities of surgical data to generate two or more modalities of time-synchronized surgical data. Next, the process converts each modality of the time-synchronized surgical data into a corresponding array of values of a common format. The process then combines the two or more arrays of values corresponding to the two or more modalities to generate a combined set of values. The process subsequently performs comprehensive data analytics on the combined set of values to generate a surgical decision for the surgical procedure.

In some embodiments, the two or more modalities of surgical data include at least two modalities of surgical data selected from the following three modalities of surgical data: video data; image data; and audio data.

In some embodiments, the image data comprise one or more of: a set of X-ray images; a set of computed tomography (CT) images; a set of magnetic resonance imaging (MRI) images; a set of ultrasonic images; and other forms of radiographic images.

In some embodiments, the video data comprise one or more of: an endoscopy surgical video; and a surgical procedure video captured by an operating room camera.

In some embodiments, the audio data include an audio recording of a surgeon narrating or discussing the surgical procedure in real-time during the surgical procedure.

In some embodiments, the surgeon discussing the surgical procedure includes discussing concerns regarding one or more of the following: an unusual anatomy of a patient; an occurrence of a complication event, such as smoking or bleeding; a landmark event of the surgical procedure; and an anomaly in the surgical procedure.

In some embodiments, the process time-synchronizes the two or more modalities of surgical data by: determining a starting time and an ending time of a target surgical event during the surgical procedure; selecting a first segment of surgical data from a first modality of the two or more modalities of surgical data between the determined starting time and ending time; selecting a second segment of surgical data from a second modality of the two or more modalities of surgical data between the determined starting time and ending time; and combining the selected first segment and second segment of surgical data for subsequent data processing and data analytics.

In some embodiments, the first modality is a surgical video, and the process selects the first segment of surgical data from the first modality by selecting a video segment between the determined starting time and ending time from the surgical video. Moreover, the second modality is an audio recording, and the process selects the second segment of surgical data from the second modality by selecting an audio segment between the determined starting time and ending time from the surgical audio.

In some embodiments, the process combines the selected video segment and the selected audio segment with a set of intra-op images captured between the determined starting time and ending time for subsequent data processing and data analytics.

In some embodiments, the process time-synchronizes the two or more modalities of surgical data by: determining a timestamp in the surgical procedure corresponding to a target surgical event; selecting a first segment of surgical data from a first modality of the two or more modalities of surgical data around the determined timestamp; selecting a second segment of surgical data from a second modality of the two or more modalities of surgical data around the determined timestamp; and combining the selected first segment and second segment of surgical data for subsequent data processing and data analytics.

In some embodiments, the common format includes one of: an alphanumeric format; and a text format.

In some embodiments, the process converts each modality of the time-synchronized surgical data into a corresponding array of values of the common format by using a corresponding machine-learning model to extract a corresponding set of text or alphanumeric values representing a set of surgical metrics from the modality of the time-synchronized surgical data.

In some embodiments, the combined set of values is a comprehensive feature set of text or alphanumeric values which represent the surgical procedure more accurately than each array of values within the combined set of values.

In some embodiments, the process receives the two or more modalities of surgical data by: (1) receiving an endoscopy video which captures an anatomy containing a tumor tissue from inside of a patient's body, wherein the tumor tissue is not easily identifiable in the captured anatomy; and (2) receiving a set of radiographic images, such as CT images which captures the anatomy from outside of a patient's body, wherein the tumor tissue is easily identifiable in the set of radiographic images. The process subsequently performs the comprehensive data analytics on the combined set of values includes by translating an identifiable location of the tumor tissue in the set of radiographic images to a corresponding location on the anatomy within the endoscopy video.

In some embodiments, the endoscopy video is a real-time endoscopy video feed, and the set of radiographic images is captured at the same time when the endoscopy video is being capturing. The process further includes highlighting the translated location of the tumor tissue on the anatomy in the real-time endoscopy video feed.

BRIEF DESCRIPTION OF THE DRAWINGS

The structure and operation of the present disclosure will be understood from a review of the following detailed description and the accompanying drawings in which like reference numerals refer to like parts and in which:

FIG. 3 presents a flowchart illustrating an exemplary process for performing a time-synchronized multi-modality data analytics for a surgical procedure in accordance with some embodiments described herein.

DETAILED DESCRIPTION

Figure 1:
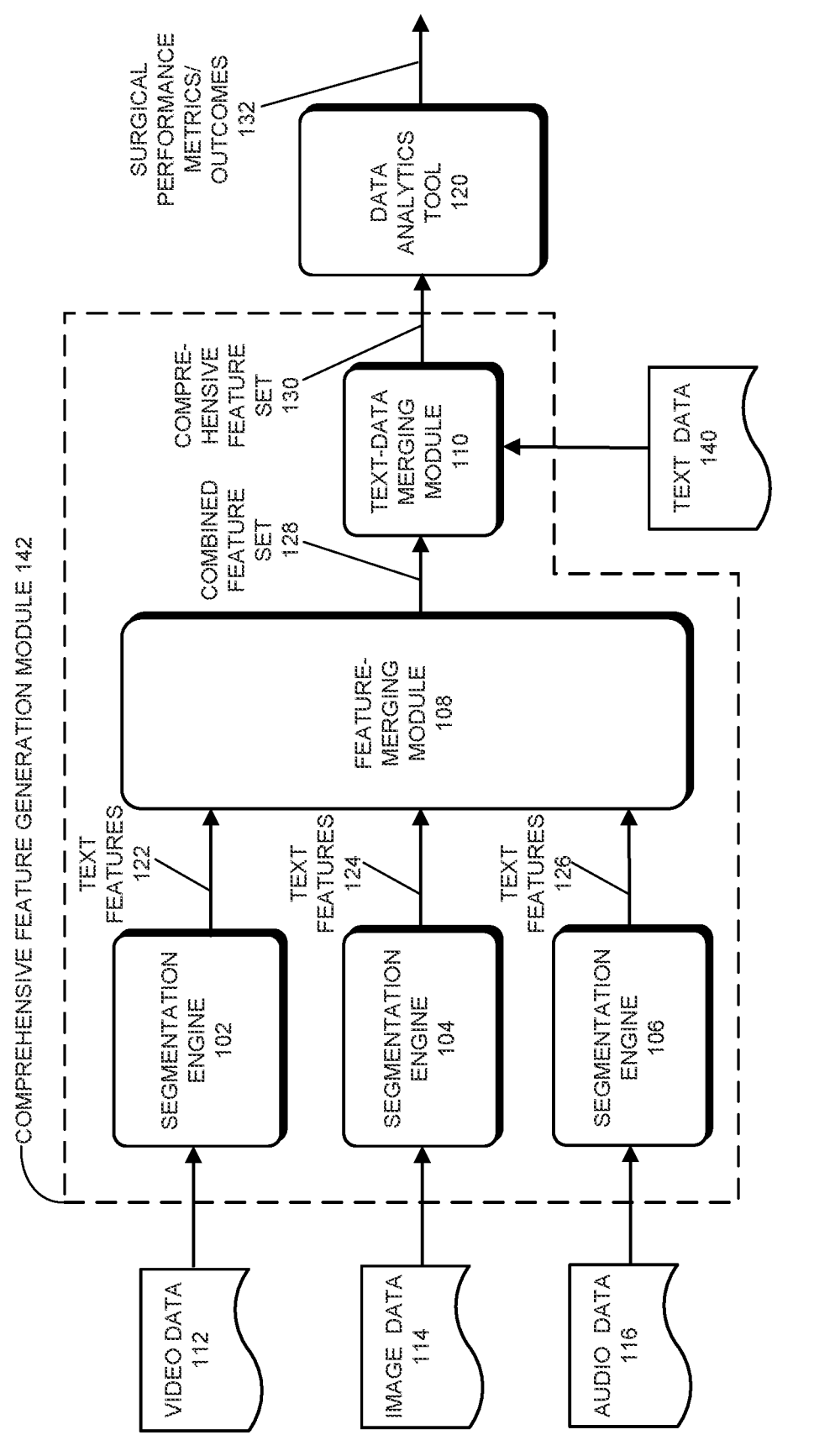
FIG. 1 shows a block diagram of an exemplary multi-modality surgical data analytics system in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Throughout the specification, the term "text data" or "text features" can include pure letter-based data or features, pure number-based data or features, and combined letter-number-based data or features. The combined letter-number-based data or features are also referred to as alphanumeric data or alphanumeric features hereinafter.

This patent disclosure provides various embodiments of combining multiple modalities of non-text data of different formats, in particular in forms of videos, images, and audios in a meaningful manner so that the combined data from the multiple modalities are compatible with text data. In some embodiments, the combined data includes a set of N text features in an N-dimensional feature space. For example, for surgical applications, the set of N text features can include a set of surgical metrics/measurements in text format. Next, the combined data can be further combined with available text data from various sources to generate a comprehensive data set which can be understood and processed by text-based data analytics tools.

In some embodiments, before combining the multiple modalities of non-text data with text data, each modality of data in the multiple modalities is first segmented and converted to a set of text features. In one or more embodiments, a different machine-learning-based segmentation engine (or simply "segmentation engine" hereinafter) can be constructed to perform the corresponding data segmentation and conversion for a different modality of data. For a particular application, such as a surgical application for example, there can be at least three segmentation engines designed for three commonly known modalities, i.e., video data, image data, and audio data, respectively. However, for a same modality of data (e.g., video data) but different applications associated with different metrics and parameters (e.g., a surgical application and a security application), different segmentation engines need to be constructed and then employed to convert the same modality of data of the different applications, respectively.

In some embodiments, once a given modality of data has been converted to a set of corresponding text features, the set of text features can be combined with other sources of text data, including text features converted from other modalities of non-text data and original text data. Once all of the available modalities of data have been converted to the text features and combined with other sources of text data, the combined feature set can then be used to perform a comprehensive data analytics using existing text-based data analytics tools. By supplementing the original text data with the multiple modalities of non-text data, the outputs from data-analytics tools, such as predictions or decisions generated based on the proposed comprehensive data analytics can be significantly more accurate than the predictions or decisions generated based on analyzing just one modality of data or just the text data alone. While the proposed data analytics techniques are described below in the context of surgical data analytics, the proposed data analytics techniques are generally applicable to various other data analytics applications, including various other healthcare-based applications.

For a surgery application which includes a surgical procedure performed within an operating room (OR), all sorts of text data can be collected. For example, different vital signs of the patient are usually continuously monitored and recorded to form a part of the text data for the surgery, while other sources of text data can include patient information, provider information, surgeon information, and hospital information. Besides the various sources of text data, non-text surgical data can generally include video data, image data, and audio data. Image data associated with a surgery procedure can include various types of image data collected from various imaging processes such as from X-ray imaging, CT scans, MRI scans, and ultrasonic scans. Moreover, each type of image data can be generated during a preoperative (or "pre-op" hereinafter) preparation/planning stage of the surgery or from an intraoperative (or "intra-op" hereinafter) imaging process during the surgery. Image data can also include snapshots grabbed from surgical video (e.g., endoscope video) data. For tumor-removal surgeries, image data can be used to determine the location and size of a tumor and the type of imaging used. Another common form of non-text surgical data-video data associated with a surgery procedure can include endoscopy procedure videos of the actual surgical procedure captured by an endoscope camera inside patient's body, and also surgical procedure videos captured by one or more OR cameras installed near (e.g., directly above) the surgical site. Yet another common form of non-text surgical data-audio data associated with a surgery procedure can include recorded audios of a surgeon narrating/discussing the surgical procedure, such as regarding an anatomy, an anomaly, an event, a complication, among others.

Note that although surgical videos are rich in medical information, using the video data alone without collaborating with other modalities of surgical data can often lead to incorrect conclusions. For example, if we want to compare the performances of two surgical procedures A and B based exclusively on the available surgical videos, then a naive analysis will extract and compare the durations of different surgical phases and the overall durations of the two procedures captured by the relevant surgical videos. It would be tempting to conclude that procedure A which completes each surgical phase and the overall procedure on time is the better performed procedure; whereas procedure B which takes much longer than expected in one or more surgical phases and/or the overall procedure is the poorer performed procedure. However, if patient from procedure B went home and quickly recovered from the surgery without any complication, whereas patient from procedure A went home, and ended up being readmitted into hospital within a week due to deteriorating health condition, then procedure B is most-likely the better performed procedure, whereas procedure A is the poorer performed procedure.

Hence, for certain complex metrics associated with a surgical application (e.g., a relationship between the surgical procedure and the surgical outcome), performing data analytics on the video data alone often fails to draw the correct conclusions on the metrics. Consequently, to predict the surgical outcome with high accuracy, additional modalities of data other than surgical videos would also be needed. These additional modalities of data can include pre-op imaging data and/or intra-op imaging data, e.g., for determining if a tumor has been detected, and location and size of a detected tumor. The additional modalities of data can also include audio data recorded during the surgical procedure, e.g., when the surgeon was narrating certain surgical steps. For example, the narration from the surgeon may expressively indicate a concern, such as indicating that the patient has an unusually large anatomy or an occurrence of a complication event such as smoking or bleeding, which could be used to explain a longer than usual surgical step or overall surgical procedure. Moreover, the additional data can also include text data collected during one or more of the pre-op, the intra-op, and the postoperative (or "post-op" hereinafter) time periods, such as all the vital data collected from monitoring the patient during a post-op time period. In some embodiments, to collect a full spectrum of data for surgery analytics, the different modalities of surgical data can be collected from the moment when the patient comes to the hospital for the first consultation to the moment when the patient is completely cured from the illness.

While the above example illustrates the deficiencies of using only video data to draw conclusions for some surgery-related metrics, it is generally not sufficient to use just one or two modalities of data (such as just videos, or just images, or just audios, or just text, or just videos with text) out of the four common modalities, i.e., videos, images, audios, and text to correctly predict certain surgical-performance metrics. Instead, a more comprehensive collection of data combining multiple modalities of surgical data should be used to draw more accurate conclusions for these surgical-performance metrics. For example, a more comprehensive collection of data can include the pre-op and intra-op image data, the intra-op endoscope videos, and intra-op audios of surgeon's narrations, and various pre-op, intra-op, and post-op text data. In some embodiments, combining different modalities of data in a meaningful way requires first converting each modality of data into a common format. In a particular embodiment, this includes converting each non-text modality of data into a set of text features. Next, the converted multiple sets of text features from the multiple non-text modalities of data can be combined with original text data because they all have a common format. Finally, a proper data analytics tool can be applied to the combined data to make correct or more accurate predictions on certain surgical-performance metrics.

In some embodiments, to convert multiple modalities of data into a common format, a separate segmentation engine is constructed for each modality of data. For example, a video segmentation engine for converting endoscope videos into text can be constructed. In some embodiments, the video segmentation engine can first segment an endoscope video into a set of video segments corresponding to a set of surgical phases and/or steps, and then extract one or more surgical metrics and parameters, such as timing information, and tool usage information from each video segment in the set of video segments.

Additionally, an audio segmentation engine for converting audios (e.g., based on various natural-language processing techniques) into text can be constructed to process audio files of surgeon's narrations/discussions. For example, the audio segmentation engine can first segment a procedure audio into a set of surgical phases and/or steps based on the segmentation outputs from the above-described video segmentation engine. Next, the audio segmentation engine can extract surgery-related metrics and parameters, such as concerns of unusual anatomies, complications, and landmark events expressed by the surgeon from the set of audio segments. Furthermore, an image segmentation engine for converting images into text can be constructed to segment pre-op and/or intra-op images and extract surgical related metrics and parameters such as the location and the size of a tumor in a given image. Besides the above three data segmentation engines, additional segmentation engines can be constructed for converting other modalities of data into text, wherein the other modalities can include certain 3D-images and holographic images.

FIG. 1 shows a block diagram of an exemplary multi-modality surgical-data analytics system 100 in accordance with some embodiments described herein. As can be seen in FIG. 1, multi-modality surgical data analytics system 100 (also referred to as "data analytics system 100" or "surgical-data analytics system 100" hereinafter) includes a set of data segmentation engines 102-106, a feature-merging module 108, a text-data merging module 110, and a data analytics tool 112, which are coupled to each other in the illustrated order. Moreover, data segmentation engines 102-106, feature-merging module 108, and text-data merging module 110 form a comprehensive feature generation module 142.

As can be seen in FIG. 1, surgical-data analytics system 100 receives video data 112, image data 114, and audio data 116 as inputs. Video data 112 can include endoscopy procedure videos capturing during the actual surgical procedure, and surgical procedure videos captured by one or more OR cameras installed near (e.g., directly above) the surgical site. Moreover, video data 112 can include both real-time video feed (if the data analytics is performed in real-time during the surgical procedure) and offline videos (if the data analytics if performed after the surgical procedure). Image data can include X-ray images, CT images, MRI images, ultrasonic images, among others, and each type of image data can be generated from a pre-op preparation/planning stage of the surgical procedure, from intra-op real-time imaging, or from a post-op time period after the surgical procedure. Moreover, image data 114 can include both real-time images (if the data analytics is performed in real-time during the surgical procedure) and offline images (if the data analytics if performed after the surgical procedure). Audio data 116 for a surgery procedure can include recorded audio files of a surgeon narrating/discussing the surgical procedure, such as regarding an anatomy, an event, a complication, among others.

Surgical-data analytics system 100 also includes a set of machine-learning-based segmentation engines 102-106 for converting each of video data 112, image data 114, and audio data 116 into a corresponding set of text features. More specifically, each of segmentation engines 102-106 is configured to segment a corresponding modality of surgical data 112-116 and extract a corresponding set of text features 122-126 from the corresponding surgical data. For example, segmentation engine 102 can be configured to convert a video segment in video data 112 into a first array of alphanumeric values representing the anatomy shown in the video segment. Meanwhile, segmentation engine 104 can be configured to convert a set of radiographic images in image data 114 into a second array of alphanumeric values representing one or more objects detected in the set of radiograph images. Moreover, segmentation engine 106 can be configured to convert an audio clip in audio data 116 into a third array of alphanumeric values representing an anatomy, a concern, a complication, or a landmark event extracted from the surgeon's narration/discussion.

In some embodiments, each set of extracted text features 122-126 is composed of a set of metrics representative of a particular surgical procedure, wherein the metrics in the set of metrics are represented as text or alphanumeric values. For example, text features 122 generated by video-data segmentation engine 102 can include a set of metrics including: (a) times taken for various surgical phases and steps; (b) a set of skill metrics which can be represented as text or numerical bins; (c) quantifications of anomalous anatomy, such as the location, size, and other measures of each detected anomaly, such as a tumor; (d) the number of times a given surgical tool was used; (e) tool idle times inside the anatomy; (f) quantifications of bleeding events; and (g) quantifications of smoke events. Text features 124 generated by image-data segmentation engine 104 can include a set of metrics including quantifications of anomalous anatomy (e.g., a tumor tissue) that are shown in patient's radiographic images, such as the location, size, and other measures of each detected anomaly. Text features 126 generated by audio-data segmentation engine 106 can include a set of metrics including flagging of unusual events (such as complications) or anatomy (e.g., unusually large anatomy) transcribed from surgeon's narration/conversations as text.

In various embodiments, each of segmentation engines 102-106 can include a machine-learning model constructed based on a regression model, a deep neural network-based model, a support vector machine, a decision tree, a Naive Bayes classifier, a Bayesian network, or a k-nearest neighbors (KNN) model. In some embodiments, each of these machine-learning models is constructed based on a convolutional neural network (CNN) architecture, a recurrent neural network (RNN) architecture, or another form of deep neural network (DNN) architecture.

Going back to FIG. 1, note that feature merging model 108 is configured to receive the three sets of text features 122-126 from segmentation engines 102-106 and subsequently combine the set of features from the multiple modalities to generate a combined feature set 128 in an N-dimensional feature space. In some embodiments, for a given surgical procedure, the combined feature set 128 in the N-dimensional feature space is a combined set of N surgical metrics representative of the surgical procedure, wherein the set of N surgical metrics are represented as text or alphanumeric values.

The combined feature set 128 in the N-dimensional feature space is then received by text-data merging module 110, which is configured to combine the combined feature set 128 with available text data 140 associated with the surgical procedure from multiple data sources to form a comprehensive feature set 130 for the surgical procedure. Note that comprehensive feature set 130 is also composed of a set of text features. Also note that data segmentation engines 102-106, feature-merging module 108, and text-data merging module 110 form comprehensive feature generation module 142, which is configured to combine multiple modalities of non-text surgical data with multiple sources of text-based surgical data into a comprehensive set of text features 130.

Finally, data analytics tool 120 is configured to receive comprehensive feature set 130, perform data analyses on the received text data, and output one or more surgical performance metrics or outcomes 132 for the surgical procedure. In some embodiments, data analytics tool 120 is a text-data analytics tool designed to process alphanumeric or text data. In a particular surgical procedure to remove a tumor, surgical performance metrics or outcomes 132 can include such metrics as whether the surgeon has correctly identified and subsequently removed the tumor, or whether the surgeon fails to correctly identify the location of tumor and unable to remove the tumor. Note that outputting surgical performance metrics/outcomes 132 can include providing visualizations of the surgical performance metrics/outcomes 132.

The disclosed surgical-data analytics system 100 can be used to solve some traditionally difficult surgical problems that do not have effective automated solutions. For example, during a surgical procedure to remove a target tumor tissue, the surgeon uses an endoscope camera inside the patient's body trying to locate the target tumor tissue. While endoscope camera captures the anatomy inside the patient's body, tumor tissue typically cannot be easily identified from endoscope images because tumor tissue often does not look particularly different from the surrounding tissues. To help real-time determining the location of the tumor, intra-op CT images can be taken in real-time within the OR over the region of the tumor within the patient's body, wherein the tumor generally stands out in the CT images. It would be ideal to have a computer program which automatically translates the location of the tumor in the CT images to a corresponding location in the endoscope images and highlights the location on the endoscope feed in real-time.

However, in practice it is extremely difficult to automatically translate certain object detected in the CT scan, such as a tumor tissue to a corresponding location within endoscope images. In fact, accurately translating a particular location or an angular direction within the CT scan to a corresponding location or an angular direction in the endoscope video is a problem that remains to be solved. A main source of the translation difficulty is that the two imaging systems use two completely different coordinate systems which do not match each other: CT images are taken from outside the patient's body whereas the endoscope images are captured from inside the patient's body. Moreover, the orientation and hence the imaging coordinate axes of the endoscope camera can be vertical, horizontal or at an arbitrary angle depending on the surrounding anatomy, and they can also constantly change as the endoscope camera navigates within the anatomy. Note that the above-described translation problem is not limited to intra-op CT scan. The same translation problem exists when an intra-op X-ray scan or an intra-op ultrasonic scan is used in place of the intra-op CT scan.

Using the disclosed surgical-data analytics system 100, multiple modalities of data including the intra-op CT images, an endoscope video segment captured during the intra-op CT scan, audio narration/discussion recorded during the intra-op CT scan can be converted into text features (e.g., which can include the location and size of the tumor) and combined into a N-dimensional text feature set. The N-dimensional text feature set combined with other relevant text data can be processed by a machine-learning model designed to translate the location of the tumor in the CT images to a corresponding location on the anatomy in the endoscope video. The output of the machine-learning model can also include a performance metric representing how well the surgeon has performed, such as whether the surgeon has correctly identified and subsequently removed the tumor, or whether the surgeon fails to correctly identify the location of tumor and unable to remove the tumor. Over time the machine-learning model can be recursively trained and improved based on the performance of the data analytics system 100.

In order to combine different modalities of data in a more meaningful manner, multiple modalities of data, e.g., video data, image data, audio data can be synchronized based on time (or "time-synced"). For example, if segmentation engine 106 for audio data can detect an event (e.g., locating a tumor in an anatomy) being discussed in an audio at, e.g., to timestamp, and segmentation engine 102 also detects the same event in an endoscope video at the same time mark, then a segment of the video and a segment of audio around to timestamp can be meaningfully combined. Moreover, if there are additional intra-op imaging taking place (e.g., CT scans taken with a mobile CT scanner or ultrasonic scans taken with an ultrasonic device) at to timestamp, these images can be meaningfully combined with the segment of the video and the segment of audio around to timestamp for making a collaborative decision, e.g., to determine the location of the tumor within an anatomy of the endoscope video with high confident.

In some embodiments, combining multiple modalities of data in a more meaningful manner can include synchronizing (or "syncing") the multiple modalities of data based on an easily identifiable time event associated with a particular modality. For example, let's assume that an intra-op imaging process begins at to and takes 2 minutes to complete from $t_0$ to $t_0$+2-min, and there is also a corresponding audio that describes the surgical procedure, then it becomes more meaningful to combine the resulting intra-op images with a segment of audio from $t_0$ to $t_0$+2-min. Moreover, if there is also a corresponding endoscope video during the same time period of $t_0$ to $t_0$+2-min, it would be more beneficial to also combine the video clip from the same 2-minute segment with the corresponding imaging and audio data. Moreover, if there are also text data generated at the same time periods, those text data can also be meaningfully combined with the other modalities of data of the same time period.

Figure 2:
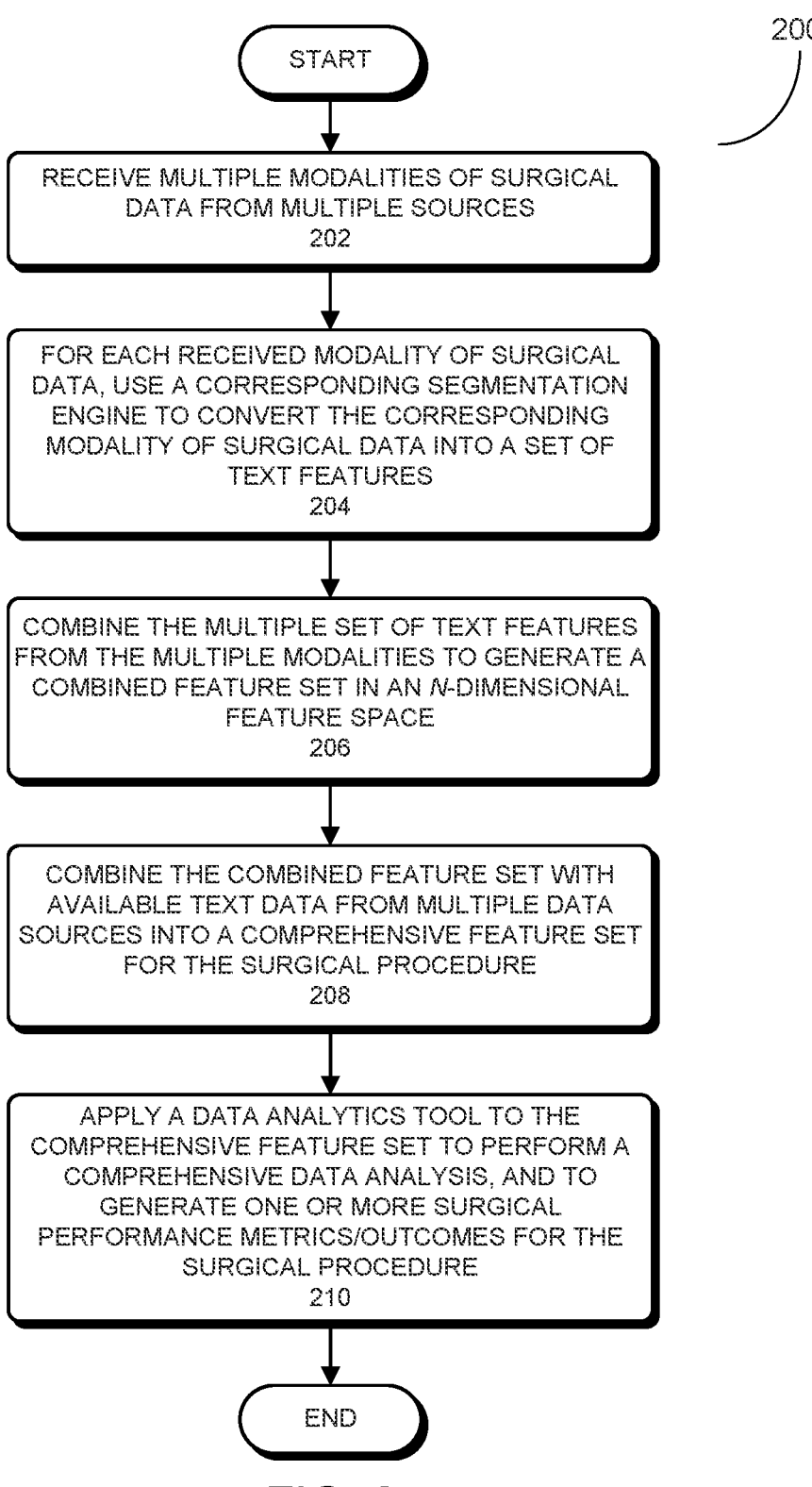
FIG. 2 presents a flowchart illustrating an exemplary process for combining multiple modalities of surgical data into a text feature space for performing comprehensive data analytics in accordance with some embodiments described herein.

FIG. 2 presents a flowchart illustrating an exemplary process 200 for combining multiple modalities of surgical data into a text feature space for performing comprehensive data analytics in accordance with some embodiments described herein. In one or more embodiments, one or more of the steps in FIG. 2 may be omitted, repeated, and/or performed in a different order. Accordingly, the specific arrangement of steps shown in FIG. 2 should not be construed as limiting the scope of the technique.

Process 200 may begin by receiving multiple modalities of surgical data from multiple sources (step 202). As mentioned above, the multiple modalities of the surgical data associated with a particular surgical procedure can include, but are not limited to image data, video data, and audio data. Image data can include radiographic images such as X-ray images, CT images, MRI images, and ultrasonic images, and each type of image data can be generated from a pre-op preparation/planning stage of the surgical procedure, from intra-op real-time imaging, or from a post-op time period after the surgical procedure. Video data can include endoscopy procedure videos capturing during the actual surgical procedure, and surgical procedure videos captured by one or more OR cameras installed near the surgical site. Audio data for a surgery procedure can include recorded audio files of a surgeon narrating/discussing the surgical procedure, such as regarding an anatomy, an event, a complication, among others.

Next, for each received modality of surgical data, process 200 uses a corresponding segmentation engine to convert the corresponding modality of surgical data into a set of text features (step 204). More specifically, each segmentation engine is configured to segment the corresponding modality of surgical data and extract a corresponding set of text features from the surgical data. In some embodiments, each set of extracted text features is composed of a set of metrics representative of a particular surgical procedure, wherein the set of metrics are represented as text or alphanumeric values.

Next, process 200 combines the multiple set of text features from the multiple modalities to generate a combined feature set in an N-dimensional feature space (step 206). In some embodiments, for a given surgical procedure, the combined feature set in the N-dimensional feature space is a combined set of N metrics representative of the surgical procedure, wherein the set of N metrics are represented as text or alphanumeric values.

Process 200 next further combines the combined feature set in the N-dimensional feature space with available text data associated with the surgical procedure from multiple data sources into a comprehensive feature set for the surgical procedure (step 208). As mentioned above, the text data for a surgical procedure can include patient vital data, patient medication data, treatment plans, progress notes, various pre-op and intra-op and post-op test results in text/alphanumeric form, other patient information, surgeon information, and hospital statistics, among others. Finally, process 200 applies a data analytics tool to the comprehensive feature set to perform a comprehensive data analysis, and to generate one or more surgical performance metrics or outcomes for the surgical procedure based on the comprehensive feature set (step 210). For example, a standard data analytics tool designed to process alphanumeric or text data can be used to process the comprehensive data set.

FIG. 3 presents a flowchart illustrating an exemplary process 300 for performing a time-synced multi-modality data analytics for a surgical procedure in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Process 300 may begin by receiving a set of intra-op images generated from an intra-op imaging process during a surgical procedure of a region of interest within a patient's body (step 302). For example, the intra-op imaging process can include a CT scan; an X-ray scan; an MRI scan, an ultrasonic scan, among others. Process 300 next determines a beginning timestamp $t_1$ and an ending timestamp $t_2$ for the intra-op imaging process (step 304). Next, process 300 receives a recorded OR audio containing surgeon's narration of the surgical procedure and an endoscope video of the actual surgical procedure (step 306). Process 300 then selects an audio segment between $t_1$ and $t_2$ from the OR audio and a video segment between $t_1$ and $t_2$ from the endoscope video (step 308). Next, process 300 provides the set of intra-op images, the audio segment, and the video segment to a feature extraction engine to extract and combine multiple sets of text features into a combined set of features in an N-dimensional feature space (step 310). Note that the feature extraction engine in step 310 can be implemented with comprehensive feature generation module 142 described in conjunction with FIG. 1.

Process 300 subsequently combines N-dimensional feature set with available text data associated with the surgical procedure to form a comprehensive feature set for the surgical procedure (step 312). Finally, process 300 applies a data analytics tool to the comprehensive feature set to generate an accurate prediction of an object in the region of interest (step 314). For example, the object can be a tumor in the region of interest and the prediction can include translating the determined location of the tumor in the intra-op images to a corresponding location in the anatomy within the endoscope video. In some embodiments, if the data analytics are performed in real-time during a tumor removal procedure, the predicted location of the tumor from the data analytics outputs can be highlighted on the anatomy in the real-time endoscope video feed.

Figure 4:
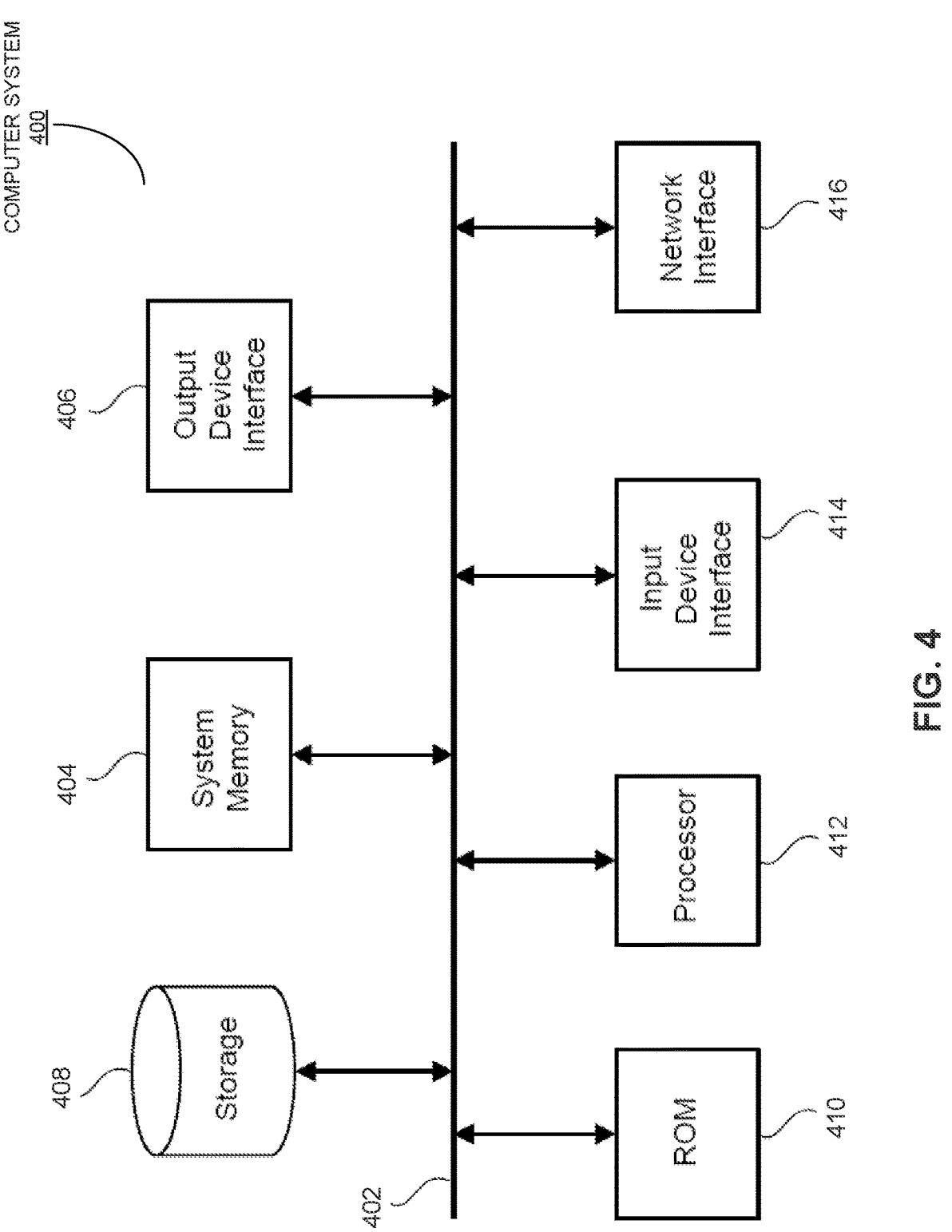
FIG. 4 conceptually illustrates a computer system with which some embodiments of the subject technology can be implemented.

FIG. 4 conceptually illustrates a computer system with which some embodiments of the subject technology can be implemented. Computer system 400 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 400 includes a bus 402, processing unit(s) 412, a system memory 404, a read-only memory (ROM) 410, a permanent storage device 408, an input device interface 414, an output device interface 406, and a network interface 416. In some embodiments, computer system 400 is a part of a robotic surgical system.

Bus 402 collectively represents all system, peripheral, and chipset buses that communicatively connect the numerous internal devices of computer system 400. For instance, bus 402 communicatively connects processing unit(s) 412 with ROM 410, system memory 404, and permanent storage device 408.

From these various memory units, processing unit(s) 412 retrieves instructions to execute and data to process in order to execute various processes described in this patent disclosure, including the above-described processes of combining multiple modalities of surgical data into a text feature space for performing comprehensive data analytics, and performing a time-synced multi-modality data analytics for a surgical procedure in conjunction with FIGS. 1-3. The processing unit(s) 412 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 412 can be a single processor or a multi-core processor in different implementations.

ROM 410 stores static data and instructions that are needed by processing unit(s) 412 and other modules of the computer system. Permanent storage device 408, on the other hand, is a read-and-write memory device. This device is a non-volatile memory unit that stores instructions and data even when computer system 400 is off. Some implementations of the subject disclosure use a mass-storage device (such as a magnetic or optical disk and its corresponding disk drive) as permanent storage device 408.

Other implementations use a removable storage device (such as a floppy disk, flash drive, and its corresponding disk drive) as permanent storage device 408. Like permanent storage device 408, system memory 404 is a read-and-write memory device. However, unlike storage device 408, system memory 404 is a volatile read-and-write memory, such as a random access memory. System memory 404 stores some of the instructions and data that the processor needs at runtime. In some implementations, various processes described in this patent disclosure, including the above-described processes of combining multiple modalities of surgical data into a text feature space for performing comprehensive data analytics, and performing a time-synced multi-modality data analytics for a surgical procedure in conjunction with FIGS. 1-3, are stored in system memory 404, permanent storage device 408, and/or ROM 410. From these various memory units, processing unit(s) 412 retrieve instructions to execute and data to process in order to execute the processes of some implementations.

Bus 402 also connects to input and output devices 414 and 406. Input devices 414 enable the user to communicate information to and select commands for the computer system. Input devices 414 can include, for example, alphanumeric keyboards and pointing devices (also called "cursor control devices"). Output devices 406 enable, for example, the display of images generated by computer system 400. Output devices 406 can include, for example, printers and display devices, such as cathode ray tubes (CRT) or liquid crystal displays (LCD). Some implementations include devices such as a touchscreen that functions as both input and output devices.

Finally, as shown in FIG. 4, bus 402 also couples computer system 400 to a network (not shown) through a network interface 416. In this manner, the computer can be a part of a network of computers (such as a local area network ("LAN"), a wide area network ("WAN"), an intranet, or a network of networks, such as the Internet. Any or all components of computer system 400 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for performing comprehensive data analytics for a surgical procedure, the computer-implemented method comprising:

time-synchronizing multiple modalities of surgical data during a surgical procedure, the multiple modalities of surgical data including a first modality of surgical data and a second modality of surgical data;

converting, by a first segmentation engine, the first modality of surgical data into a first set of alphanumeric values during the surgical procedure, the first modality of surgical data including an audio feed being captured during the surgical procedure;

converting, by a second segmentation engine, the second modality of surgical data into a second set of alphanumeric values during the surgical procedure, the second modality of surgical data including a video feed being captured during the surgical procedure;

combining the first set of alphanumeric values and the second set of alphanumeric values to generate a prediction during the surgical procedure, wherein generating the prediction includes translating an identifiable location of an event detected in the audio feed to a corresponding location of the event within the video feed; and based on the prediction, highlighting the corresponding location of the event within the video feed.

2. The computer-implemented method of claim 1, wherein the audio feed includes a surgeon narrating or discussing the surgical procedure in real-time.

3. The computer-implemented method of claim 1, wherein generating the prediction further includes determining a size of an anomaly, an occurrence of a smoking event, or an occurrence of a bleeding event.

4. The computer-implemented method of claim 1, wherein the video feed includes real-time video captured by one or more cameras inside a patient's body or near a surgical site, the one or more cameras including an endoscope camera.

5. The computer-implemented method of claim 1, further comprising:

time-synchronizing the multiple modalities of surgical data during the surgical procedure, the multiple modalities of surgical data including a third modality of surgical data;

converting, by a third segmentation engine, the third modality of surgical data into a third set of alphanumeric values during the surgical procedure; and combining the first set of alphanumeric values, the second set of alphanumeric values, and the third set of alphanumeric values to generate the prediction during the surgical procedure.

6. The computer-implemented method of claim 5, wherein the third modality is image data associated with the surgical procedure, the image data being generated from pre-op imaging, intra-op real-time imaging, and post-op imaging.

7. The computer-implemented method of claim 5 further comprising:

combining text data, the first set of alphanumeric values, the second set of alphanumeric values, and the third set of alphanumeric values to generate the prediction related to the event during the surgical procedure, wherein the text data includes patient vitals, patient information, surgeon information, hospital statistics, treatment plans, medication data, test results and progress notes.

8. A non-transitory computer-readable medium to store instructions that, when executed by a processor of a computer system, cause the computer system to:

time-synchronize multiple modalities of surgical data during a surgical procedure, the multiple modalities of surgical data including a first modality of surgical data and a second modality of surgical data;

convert, by a first segmentation engine, the first modality of surgical data into a first set of alphanumeric values during the surgical procedure, the first modality of surgical data including an audio feed being captured during the surgical procedure;

convert, by a second segmentation engine, the second modality of surgical data into a second set of alphanumeric values during the surgical procedure, the second modality of surgical data including a video feed being captured during the surgical procedure;

combine the first set of alphanumeric values and the second set of alphanumeric values to generate a prediction during the surgical procedure, wherein generating the prediction includes translating an identifiable location of an event detected in the audio feed to a corresponding location of the event within the video feed; and based on the prediction, highlight the corresponding location of the event within the video feed.

9. The non-transitory computer-readable medium of claim 8, wherein, the audio feed includes a surgeon narrating or discussing the surgical procedure in real-time.

10. The non-transitory computer-readable medium of claim 8, wherein generating the prediction further includes determining a size of an anomaly, an occurrence of a smoking event, or an occurrence of a bleeding event.

11. The non-transitory computer-readable medium of claim 8, wherein the video feed includes real-time video captured by one or more cameras inside a patient's body or near a surgical site, the one or more cameras including an endoscope camera.

12. The non-transitory computer-readable medium of claim 8, further comprising instructions that, when executed by the processor of the computer system, cause the computer system to:

time-synchronize the multiple modalities of surgical data during the surgical procedure, the multiple modalities of surgical data including a third modality of surgical data;

convert, by a third segmentation engine, the third modality of surgical data into a third set of alphanumeric values during the surgical procedure; and combine the first set of alphanumeric values, the second set of alphanumeric values, and the third set of alphanumeric values to generate the prediction during the surgical procedure.

13. The non-transitory computer-readable medium of claim 12, wherein the third modality of is image data associated with a surgical procedure, the image data being generated from pre-op imaging, intra-op real-time imaging, and post-op imaging.

14. The non-transitory computer-readable medium of claim 12 further comprising instructions that, when executed by the processor of the computer system, cause the computer system to:

combine text data, the first set of alphanumeric values, the second set of alphanumeric values, and the third set of alphanumeric values to generate the prediction related to the event during the surgical procedure, wherein the text data includes patient vitals, patient information, surgeon information, hospital statistics, treatment plans, medication data, test results and progress notes.

15. A system for performing comprehensive data analytics for a surgical procedure, the system comprising:

one or more processors; and a memory coupled to the one or more processors, wherein the memory stores a set of instructions that, when executed by the one or more processors, cause the system to:

time-synchronize multiple modalities of surgical data during a surgical procedure, the multiple modalities of surgical data including a first modality of surgical data and a second modality of surgical data;

convert, by a first segmentation engine, the first modality of surgical data into a first set of alphanumeric values during the surgical procedure, the first modality of surgical data including an audio feed being captured during the surgical procedure;

convert, by a second segmentation engine, the second modality of surgical data into a second set of alphanumeric values during a surgical procedure, the second modality of surgical data including a video feed being captured during the surgical procedure;

combine the first set of alphanumeric values and the second set of alphanumeric values to generate a prediction during the surgical procedure, wherein generating the prediction includes translating an identifiable location of an event detected in the audio feed to a corresponding location of the event within the video feed; and based on the prediction, highlight the corresponding location of the event within the video feed.

16. The system of claim 15, wherein the audio feed includes a surgeon narrating or discussing the surgical procedure in real-time.

17. The system of claim 15, wherein generating the prediction further includes determining a size of an anomaly, an occurrence of a smoking event, or an occurrence of a bleeding event.

18. The system of claim 15, wherein the video feed includes real-time video captured by one or more cameras inside a patient's body or near a surgical site, the one or more cameras including an endoscope camera.

19. The system of claim 15, further comprising instructions that, when executed by the one or more processors, cause the system to:

time-synchronize the multiple modalities of surgical data during the surgical procedure, the multiple modalities of surgical data including a third modality of surgical data;

convert, by a third segmentation engine, the third modality of surgical data into a third set of alphanumeric values during a surgical procedure; and combine the first set of alphanumeric values, the second set of alphanumeric values, and the third set of alphanumeric values to generate the prediction during the surgical procedure.

20. The system of claim 19, further comprising instructions that, when executed by the one or more processors, cause the system to:

combine text data, the first set of alphanumeric values, the second set of alphanumeric values, and the third set of alphanumeric values to generate the prediction related to the event during the surgical procedure, wherein the third modality of is image data associated with the surgical procedure, the image data being generated from pre-op imaging, intra-op real-time imaging, and post-op imaging, and text data includes patient vitals, patient information, surgeon information, hospital statistics, treatment plans, medication data, test results and progress notes.

\* \* \* \* \*